United States Patent
Greil et al.

(10) Patent No.: US 6,489,470 B1
(45) Date of Patent: Dec. 3, 2002

(54) PROCESS FOR THE PREPARATION OF CEFPODOXIME PROXETIL DIASTEREOISOMERS

(75) Inventors: Julia Greil, Alpbach (AT); Johannes Ludescher, Breitenbach (AT); Klaus Totschnig, Kundl (AT); Siegfried Wolf, Brixlegg (AT)

(73) Assignee: Biochemie Gesellschaft m.b.H., Kundl (AT)

( * ) Notice: Subject to any disclaimer, the term of this patent is extended or adjusted under 35 U.S.C. 154(b) by 0 days.

(21) Appl. No.: 09/582,896

(22) PCT Filed: Jan. 7, 1999

(86) PCT No.: PCT/EP99/00057

§ 371 (c)(1),
(2), (4) Date: Aug. 21, 2000

(87) PCT Pub. No.: WO99/35149

PCT Pub. Date: Jul. 15, 1999

(30) Foreign Application Priority Data

Jan. 9, 1998 (AT) .................................................. 21/98

(51) Int. Cl.⁷ ............................................. C07D 501/34

(52) U.S. Cl. ...................................... 540/220; 540/228

(58) Field of Search ................................ 540/228, 220

(56) References Cited

U.S. PATENT DOCUMENTS

| 4,409,215 A | 10/1983 | Takaya et al. | 424/246 |
| 4,486,425 A | 12/1984 | Nakao et al. | 424/246 |

FOREIGN PATENT DOCUMENTS

| EP | 0 076 528 | 4/1983 |
| EP | 0 531 875 A | 3/1993 |
| GB | 2 110 688 A | 6/1983 |
| WO | WO-00/66594 | * 11/2000 |

OTHER PUBLICATIONS

Hashimoto, Chem Abs. 114, 247049 (1991).*
Chemical Abstracts, vol. 125, No. 22, Nov. 25, 1996, Abstract No. 284616, Hamaura T. et al., "Gel formation of cefpodoxime proxetil", XP002102142 & S.T.P. Pharma Sci., vol. 5, No. 4, pp. 324–331.
Derwent Abstract 95–370478/48, Asahi Kasei Kogyo KK, JP 07250697, Oct. 3, 1995.
Derwent Abstract 89–019685/03, Sankyo KK, J63295–590, Jan. 12, 1988.
Fujimoto, K. et al., "Studies on Orally Active Cephalosporin Esters," The Journal of Antibiotics, vol. 40, pp. 370–384 (1987).
International Search Report PCT/EP 99/00057.

* cited by examiner

Primary Examiner—Mark L. Berch
(74) Attorney, Agent, or Firm—Hesna J. Pfeiffer

(57) ABSTRACT

A process for increasing the diastereoisomeric ratio (B/A+B), wherein B is the more apolar and A is the more polar of two diastereoisomers, of a mixture of diastereoisomers of a compound of formula

I

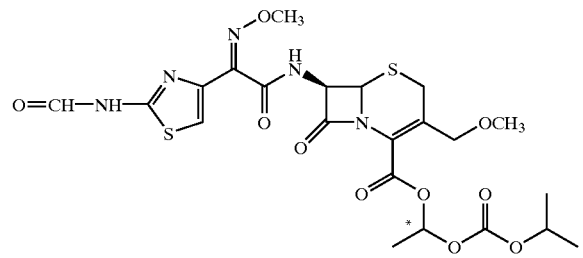

the diastereoisomers being with respect to the carbon atom marked with a star in formula I, comprising treating a mixture of diastereoisomers of a compound of formula I with alcohol and water and isolating the precipitated compound of formula I in an increased diastereoisomeric ratio (B/A+B) of 0.5 to 0.6.

11 Claims, No Drawings

PROCESS FOR THE PREPARATION OF CEFPODOXIME PROXETIL DIASTEREOISOMERS

The present invention relates to cefpodoxim proxeril of formula

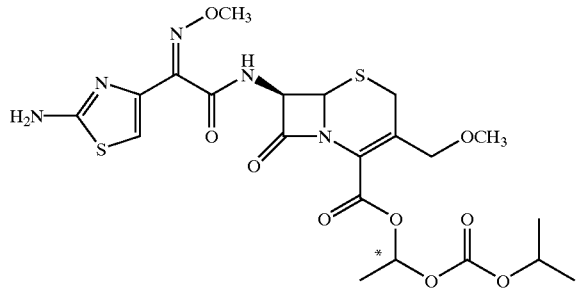

II e.g. described in The Merck Index, Twelth Edition, Item 1991, and more particularly to a process for the adjustment, e.g. change, of the diastereoisomeric ratio of the two existing diastereoisomers being with respect to the carbon atom attached to the oxygen of the ester group in the carboxyl ester group in position 4 of the ring system (marked with a star (*) in formula II). A diastereoisomeric ratio (B/A+B) of cefpodoxime proxetil currently on the market may be around 0.53. B is the more apolar of the two diastereoisomers. Because of different bioavailability of these individual diastereoisomers a commercial form for oral administration of cefpodoxim proxetil has to be within a defined ratio (B/A+B); otherwise such a form might not be bioequivalent. A diastereoisomeric ratio (B/A+B) of 0.5 to 0.6 has been found to be bioequivalent with a commercial form. Determination of the diastereoisomeric content of the diastereoisomers A and B in cefpodoxime proxetil may be carried out by HPLC, e.g. as described in Pharmacopeial Forum, Vol. 23, No. 4, p. 4388 ff (1997), the content of which is incorporated herein by reference, from which a diastereoisomeric ratio (B/A+B) and (A/A+B) may be calculated.

One process in the production of cefpodoxime proxetil may be carried out via acylation of 7-amino-3-methoxy-methyl-3-cephem-4-carboxylic acid-1-(isopropoxycarbonyloxy)ethylester of formula

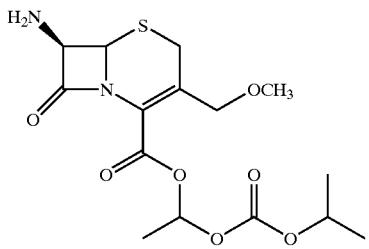

III with activated Z-2-(methoxyimino)-2-(2-formylaminothiazol-4-yl)-acetic acid to obtain N-formylcefpodoxime proxetil of formula

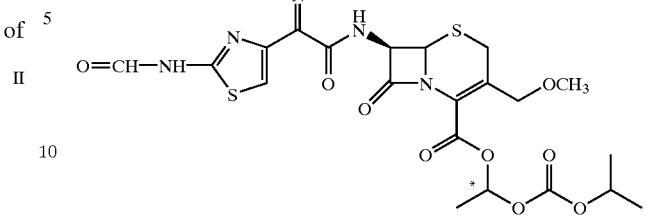

I

It was found that a mixture of diastereoisomers of a compound of formula I may be obtained in a diastereoisomeric ratio (B/A+B) of 0.48 to below 0.50. The reaction for splitting off the formyl group in a compound of formula I obtained to obtain cefpodoxime proxetil of formula II may have no significant influence on the diastereoisomeric ratio (B/A+B) and consequently (B/A+B) in cefpodoxime proxetil obtained may be outside of 0.5 to 0.6. Surprisingly a simple process has now be found wherein an appropriate diastereoisomeric ratio of the diastereoisomers of a compound of formula I may be obtained which may, result in cefpodoxime proxetil by splitting off the formyl group in a diastereoisomeric ratio which is 0.5 to 0.6.

In one aspect the present invention provides a process for the adjustment, e.g. change, of the diastereoisomeric ratio (B/A+B), wherein B is the more apolar of the two diastereoisomers, of a mixture of diastereoisomers of a compound of formula I, e.g. adjusting a diastereoisomeric ratio (B/A+B) to 0.5 to 0.6; the diastereoisomers being with respect with the carbon atom marked with a star in formula I, comprising treating a mixture of diastereoisomers of a compound of formula I, e.g. in an additive, e.g. a compound selected from an organic amide, an urea, an imidazolidinone or a pyrimidinone, e.g. a 10 to 50% (w/w) solution of a mixture of diastereoisomers of a compound of formula I in an additive; with alcohol, e.g. selecting the alcohol from $(C_{1-6})$alcohols; and water, e.g. treating a mixture of diastereoisomers of a compound of formula I with 3 ml to 10 ml alcohol and 10 ml to 30 ml water per gram of a compound of formula I.

A process according to the present invention may be carried out as follows:

A compound of formula I may be produced, e.g. in conventional manner and e.g. as follows: The carboxylic acid group in position 4 of the ring system of 7-amino-3-methoxymethyl-3-cephem-4-carboxylic acid (AMCA) which is a known compound and obtainable e.g. in conventional manner, may be esterified to obtain a compound of formula III. This may be effected e.g. in conventional manner, e.g. by reacting AMCA with a compound of formula

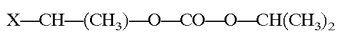

X—CH—(CH₃)—O—CO—O—CH(CH₃)₂ wherein X denotes a leaving group, e.g. a conventional leaving group, such as a halogenide, e.g. an iodide; e.g. in the presence of a solvent. Esterification may be effected e.g. in a conventional solvent, e.g. an organic solvent such as ketones, e.g. acetone, e.g. in the presence of a hydrocarbon, e.g. toluene; and e.g. in the presence of a base; e.g. an amidine, such as 1,5-diazabicyclo(4,3,0)non-5-ene (DBN) and 1,8-diazabicyclo(5,4,0)undec-7-ene (DBU); or a guanidine, e.g. a linear guanidine, such as tetramethylguanidine, pentamethylguanidine, tetraethylguanidine, tetramethylethylguanidine and tetramethylbenzylguanidine or a cyclic or bicyclic guanidine, e.g. 1,5,7-triazabicyclo-(4,4,0)-dec-5-ene, and 7-methyl, 7-ethyl, 7-benzyl and 7-phenyl derivatives thereof. A compound of formula III obtained may be isolated, if desired, e.g. in conventional manner.

The nitrogen atom in position 7 of the ring structure of a compound of formula III, e.g. obtained as described above, e.g. with or without isolation, preferably without isolation, may be acylated e.g. in conventional manner. This may be effected e.g. by reaction of a compound of formula III obtained in the esterifcation reaction, with activated Z-(2-formamidothiazol-4-yl)-methoxyimino acetic acid, e.g. including an ester and an acid halogenide, such as Z-(2-formylaminothiazol-4-yl)-methoxyimino-acetic acid chloride, e.g. in the form of a salt, e.g. a hydrochloride, including activated Z-(2-formamidothiazol-4-yl)-methoxyimino acetic acid obtainable by a Vilsmeier reaction. Vilsmeier activated Z-(2-formamidothiazol-4-yl)-methoxyimino acetic acid may be produced e.g. in conventional manner, e.g. in situ in the reaction mixture e.g. by treating Z-(2-formamidothiazol-4-yl)-methoxyimino acetic acid with phosphoroxyhalogenide, e.g. chloride, e.g. under Vilsmeier reaction conditions.

Acylation may be carried out in an organic solvent, including e.g. carboxylic acid esters, e.g. acetates, such as ethyl acetate; halogenated hydrocarbons, e.g. aliphatic, such as methylene chloride; e.g. in the presence of an amide, e.g. N,N-dimethylformamide; e.g. in the presence of pH adjustment. pH adjustment may be effected e.g. by addition of a base, such as an inorganic base, e.g. a carbonate or bicarbonate, e.g. sodium and potassium, or e.g. of an, e.g. weakly, basic anionic exchange resin, to a pH of ca. 2.5 to 8.0. A compound of formula I obtained may be isolated, e.g. in conventional manner. A mixture of diastereoisomers of a compound of formula I may be obtained in a diastereoisomeric ratio (B/B+A) of 0.47 up to below 0.5.

For adjustment, e.g. change, of the diastereoisomeric ratio of a mixture of diastereoisomers of a compound of formula I, e.g. obtained as described above, e.g. with or without isolation, preferably without isolation, e.g. a reaction mixture from acylation, e.g. as described above, may be treated with alcohol and water, e.g. in the presence of an additive, e.g. a compound which is liquid under the reaction conditions and wherein a compound of formula I may be dissolved, e.g. a compound selected from an organic amide, e.g. an amide of formic acid or acetic acid, or a cyclic amide, e.g. pyrrolidone or N-methylpyrrolidone, or an urea, e.g. tetramethylurea, or an imidazolidinone, e.g.1,3-dimethyl-2-imidazolidinone (DMEU) or a pyrimidinone, e.g.1,3dimethyl-3,4,5,6-tetrahydro-2(1H)-pyrimidinone (DMPU), or a mixture of individual additives, e.g. as described above, preferably an organic amide or an urea. An additive may be added to a reaction mixture obtained in the acylation step. From a reaction mixture obtained in the acylation step, e.g. containing an additive, e.g. added after acylation reaction to the reaction mixture, a solvent used in the acylation step which is different from an additive described above may be evaporated off, e.g. keeping the main part of an additive in the evaporation residue.

A reaction mixture obtained in the acylation step or an evaporation residue as referred to hereinafter, e.g. obtainable e.g. as described above may be a solution, an, e.g. 10 to 50% (w/w) solution, of a mixture of diastereoisomers of a compound of formula I in an additive, containing e.g. water, e.g. small amounts, e.g. originating from the acylation step, and e.g. containing amounts of organic solvent, e.g. other than an additive, e.g. organic solvent as used in the esterification and/or acylation step, e.g. from trace amounts up to 30% (w/w) in respect with a compound of formula I, e.g. depending whether, or in which extent, an evaporation step is used.

A reaction mixture obtained in the acylation step, or an evaporation residue obtained as described above, may be treated with water and alcohol, e.g. adding, e.g. dropwise or e.g. by allowing to flow an evaporation residue or a reaction mixture obtained in the acylation step to, e.g. into, a mixture of alcohol/water, or a mixture of alcohol/water to, e.g. into, an evaporation residue or a reaction mixture obtained in the acylation step, or an evaporation residue or a reaction mixture obtained in the acylation step to, e.g. into, alcohol; or alcohol to, e.g. into, an evaporation residue or a reaction mixture obtained in the acylation step; and adding, e.g. dropwise, water to, e.g. into, the mixture obtained; or adding the mixture obtained to, e.g. into, water.

Appropriate alcohols include e.g. ($C_{1-6}$)alcohols, preferably methanol and ethanol and mixtures of individual alcohols. An appropriate amount of alcohol includes preferably an amount of 3 to 10 ml, e.g. 5 to 6 ml of alcohol per gram of a compound of formula I. An appropriate amount of water includes an amount which is greater than 5 ml, e.g. 10 to 30 ml per gram of a compound of formula I.

A compound of formula I may precipitate, e.g. in amorphous, e.g. filterable form. The diastereoisomeric ratio (B/B+A) of a mixture of diastereoisomers of a compound of formula I obtained may be dependent on the alcohol/water ratio in the mixture and may increase with increasing amounts of alcohol in respect with water. An alcohol/water ratio of about 1:1 to 1:6, preferably; 1:1.5 to 1:5 may conveniently be used to obtain a mixture of diastereoisomers wherein the diastereoisomeric ratio (B/B+A) is at least 0.5 and more.

In another aspect the present invention provides a process for the production of a mixture of diastereoisomers of cefpodoxim proxetil of formula II in a diastereoisomeric ratio (B/A+B), wherein B is the more apolar of the two diastereoisomers, of 0.5 to 0.6, the diastereoisomers being with respect with the carbon atom marked with a star in formula I, comprising producing a mixture of diastereoisomers of a compound of formula I, e.g. in a diastereoisomeric ratio of below 0.5, by acylating a compound of formula III, e.g. a mixture of diastereoisomers of a compound of formula III, e.g. produced by esterifying 7-amino-3-methoxymethyl-3-cephem-4-carboxylic acid with a compound of formula

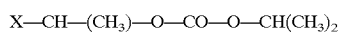

wherein X denotes a leaving group;

with activated Z-(2-formamidothiazol4-yl)-methoxyimino acetic acid, treating a mixture of diastereoisomers of a compound of formula I in an additive e.g. a compound selected from an organic amide, an urea, an imidazolidinone or a pyrimidinone, e.g. a 10 to 50% (w/w) solution of a mixture of diastereoisomers of a compound of formula I in an additive; with alcohol, e.g. selected from ($C_{1-6}$) alcohols, and water, e.g. treating a mixture of diastereoisomers of a compound of formula I with 3 ml to 10 ml alcohol and 10 ml to 30 ml water per gram of a compound of formula I; and splitting off the formyl group from the amino group attached to the thiazolyl group.

In another aspect the present invention provides a process for the production of a mixture of diastereoisomers of cefpodoxim proxetil of formula II in a diastereoisomeric ratio (B/A+B), wherein B is the more apolar of the two diastereoisomers, of 0.5 to 0.6, the diastereoisomers being with respect with the carbon atom marked with a star in formula II, characterized by the following steps
 i) esterifying 7-amino-3-methoxymethyl-3-cephem-4carboxylic acid with a compound of formula

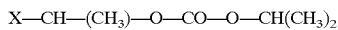

wherein X denotes a leaving group in the presence of a solvent, e.g. and in the presence of a base;
 ii) acylating the amine group in position 7 of the ring system of a compound of formula III obtained in step i) with activated Z-(2-formamidothiazol-4-yl)-methoxyimino acetic acid, e.g. a halogenide, e.g. in the presence of a base;
 iii) adding a compound selected from an organic amide, an urea, an imidazolidinone or a pyrimidinone to a reaction mixture obtained in step ii) and evaporating off a solvent used in the acylation step, and
 iv) treating the evaporation residue obtained in step iii) with alcohol and water.

In a further aspect the present invention provides a process for the isolation of 7-[2-(2-formylaminothiazol-4-yl)-2-(Z)-(methoxyimino)-acetamido]-3-methoxyimino-3-cephem-4-carboxylic acid-1-(isopropoxy-carbonyloxy)-ethylester (as a diastercoisoineric mixture) of formula I; e.g. after the reaction of the compound of formula III with activated derivative of Z-2-(methoxyimino)-2-(2-formylaminothiazol-4-yl)-acetic acid in a solvent, characterised in that to the solution of the compound of formula I is added an organic amide, a urea, 1,3-dimethyl-2-imidazolidinone (DMEU) or 1,3-dimethyl-3,4,5,6-tetrahydro-2(1H)-pyrimidinone (DMPU), the solvent is subsequently removed by evaporation and the residue of evaporation is mixed with water/alcohol.

A process according to the present invention is useful for the production of cefpodoxime proxetil in a diastereoisomeric ratio (B/A+B), wherein B is the more apolar of the two diastereoisomers, of 0.5 to 0.6. A diastereoisomeric ratio (B/A+B) of 0.5 to 0.6 of cefpodoxime proxetil, e.g. in a pharmaceutical composition, is bioequivalent to cefpodoxime proxetil, e.g. in a pharmaceutical composition, currently on the market. Cefpodoxime proxetil produced according to the present invention may thus be used in the same dosages to and in the same indications as cefpodoxime proxetil currently on the market.

In the following examples, which illustrates the invention more fully, but should in no way limit its scope, all temperatures are given in degrees Celsius.

The following abbreviations are used:
DBU 1,8-diazabicyclo[5.4.0]undec-7-ene
DMF=N,N-dimethylformamide
TMG=tetramethylguanidine
AMCA=7-amino-3-methoxymethyl-3-cephem4-carboxylic acid Determination of the diastereoisomeric content A and B in a compound of formula III, I and cefpodoxim proxetil may be carried out by HPLC, e.g. analogously, as described in Pharmacopeial Forum, Vol. 23, No. 4, p. 4388 ff (1997), from which a diastereoisomeric ratio (B/A+B) and (A/A+B) may be calculated.

EXAMPLE 1 a) 7-Amino-3-methoxymethyl-3-cephem-4-carboxylic Acid-1-(isopropoxycarbonyloxy)ethyl) Ester A suspension of 30 g of AMCA in 300 ml of acetone is mixed with 18.6 g of DBU and stirred for 15 minutes at room temperature. The solution obtained is cooled to ca. 0° and mixed over the course of ca. 15 minutes with 261 g of a 14% toluene solution of 1-iodoethylisopropyl carbonate. Stirring is continued fro ca. 4 hours at ca. 0° and the solution obtained is poured onto a mixture of 600 ml of water and 21 ml of conc. HCl. The pH of the mixture obtained is adjusted to ca. 1.0. The aqueous phase is extracted with 200 ml of hexane, mixed with 700 ml of ethyl acetate and a pH of ca. 8.2 is adjusted by addition of 5N NaOH. A two-phase system is obtained and the organic phase is extracted with an aqueous saturated NaCl solution, dried over $MgSO_4$, and filtered. A solution of 7-amino-3-methoxymethy-3-cephem-4-carboxylic acid-1-(isopropoxycarbonyloxy)ethyl ester in ethyl acetate is obtained. Diastereoisomeric ratio B/(A+B)= 0.49.

b) 7-[2-(2-formylaminothiazol-4-yl)-2-(Z)-(methoxyimino)acetamido]-3-methoxymethyl-3-cephem-4-carboxylic Acid-1-(isopropoxycarbonyloxy)ethyl Ester A solution of 37.4 g of 7-amino-3-methoxymethyl-3-cephem-4-carboxylic acid-1-(isopropoxycarbonyloxy)ethyl ester with a diastereoisomeric ratio B/(A+B) of 0.49 in 689 ml of ethyl acetate is cooled with ice water. At a temperature of ca. 2–3°, 0.105 mols of Z-(2-formamidothiazol-4-yl)-methoxyimino-acetyl chloride hydrochloride are added in portions over the course of ca. 25 minutes, and the mixture obtained is stirred for ca. further 10 minutes. The pH is simultaneously adjusted to ca. 6.5 to 7.3 by addition of a solution of 18.48 g of sodium bicarbonate in 345 ml of water. Stirring is continued for ca. 1 hour. A two phase system is formed and the phases are separated; the organic phase is mixed with 350 ml of water and the pH of the mixture obtained is adjusted to ca. 7.4 by addition of a saturated sodium bicarbonate solution. The phases formed are separated and the organic phase is washed with 350 ml of water, mixed with 117 ml of DMF and concentrated by evaporation on a rotary evaporator at 40°/100 mbar until no further ethyl acetate is distilling off. An evaporation residue is obtained containing 7-[2-(2-formylaminothiazol-4-yl)-2-(Z)-(methoxylimino)acetamido]-3-methoxymethyl-3-cephem-4-carboxylic acid-1-(isopropoxycarbonyloxy)ethyl ester in a diastereoisomeric ratio (B/A+B) of 0.49. The evaporation residue is divided into portions. 7-[2-(2-formylaminothiazol-4-yl)-2-(Z)-(methoxyimino) acetamido]-3-methoxymethyl-3-cephem-4-carboxylic acid-1-(isopropoxycarbonyloxy)ethyl ester is precipitated as follows:

Portions, 37 g each, of the evaporation residue are treated with the amount of ethanol as set out under "ml ethanol" in TABLE 1 below, and, over the course of ca. one hour, the amount of water as set out under "ml water" in TABLE 1 below is added dropwise whilst stirring. 7-[2-(2-formylaminothiazol-4-yl )-2-(Z)-(methoxyimino) acetamido]-3-methoxymethyl-3-cephem-4-carboxylic acid-1-(isopropoxycarbonyloxy)ethyl ester precipitates. The suspension obtained is stirred for ca. further 30 minutes at room temperature, the precipitate is isolated, (isolation capability characteristic as set out in TABLE 1; "very good" means that the precipitate is very easily filterable, "good" means that the precipitate is easily filterable, "average" means that the precipitate is filterable and "poor" means that the precipitate is badly filterable) below through a suction filter, washed with water and dried over phosphorus pentoxide overnight at 40–45° in a drying chamber. 7-[2-(2-formylaminothiazol-4-yl)-2-(Z)-(methoxyimino)-acetamido]-3-methoxymethyl-3-cephem-4-carboxylic acid- 1-(isopropoxycarbonyloxy)ethyl ester in a diastereoisomeric ratio (B/A+B) as set out in TABLE 1 below is obtained:

TABLE 1

| experiment | ml ethanol | ml water | diastereoisomeric ratio (B/A + B) | isolating capability |
|---|---|---|---|---|
| A | 58.5 | 292.5 | 0.508 | good |
| B | 58.5 | 146.2 | 0.524 | average |
| C | 58.5 | 117 | 0.541 | average |
| D | 74 | 292.5 | 0.512 | very good |
| E | 74 | 370 | 0.508 | very good |
| comparison | 0 | 370 | 0.491 | poor | c) 7-[2-(2-Aminothiazol-4-yl)-2-(Z)-(methoxyimino) acetamido]-3-methoxymethyl-3-cephem-4-carboxylic Acid-1-(isopropoxycarbonyloxy)ethyl Ester 5 g of each of the compounds obtained according to experiments A to B and comparison experiment as set out in TABLE 1 above, are added to a mixture of 35 ml of methanol and 0.6 ml of conc. sulphuric acid. The mixture is stirred for ca. 90 minutes and slowly added during ca. 25 minutes to a mixture of 2.1 g of sodium bicarbonate and 400 ml of water. 7-[2-(2-aminothiazol-4-yl)-2-(Z)-(methoxyimino)acetamido]-3-methoxymethyl-3-cephem-4-carboxylic acid-1-(isopropoxycarbonyloxy)ethyl ester precipitates. The suspension obtained is stirred for ca. one hour and the precipitate is isolated through a suction filter, washed with water and dried over phosphorus pentoxide overnight at ca. 35° in a vacuum. 7-[2-(2-aminothiazol-4-yl)-2-(Z)-(methoxyimino)acetamido]-3-methoxymethyl-3-cephem-4-carboxylic acid-1-(isopropoxycarbonyloxy)ethyl ester (cefpodoxime proxetil) is obtained in a diastereoisomeric ratio (B/A+B) as set out in TABLE 2 below:

TABLE 2

| experiment | diastereoisomeric ratio (B/A + B) |
|---|---|
| A | 0.511 |
| B | 0.528 |
| C | 0.544 |
| D | 0.515 |
| E | 0.526 |
| comparison | 0.493 |

EXAMPLE 2 a) Vilsmeier Activation of Z-(2-Formamidothiazol-4-yl)-methoxyimino)-acetic Acid A mixture of 200 ml of ethyl acetate and 54 ml of DMF is cooled to ca. −10°, treated with 10.06 ml phosphoroxychloride (0.11 mol) and stirred for ca. 1 hour at ca. −10°. The mixture obtained is cooled to ca. −15° and 26.36 g (0.115 mol) of Z-(2-formamidothiazol-4-yl)-methoxyimino)-acetic acid are added. The mixture obtained is stirred for ca. 1 hour at ca. −10° and cooled to ca. −25° and contains (Vilsmeier) activated Z-(2-formamidothiazol-4-yl)-methoxyimino)-acetic acid.

b) 7-[2-(2-Formylaminothiazol-4-yl)-2-(Z)-(methoxyimino)acetamido]-3-methoxylmethyl-3-cephem-4-carboxylic Acid-1-(isopropoxycarbonyloxy)ethyl Ester 33.6 g of sodium bicarbonate in 748 ml of water are added to 558 ml of a solution of 0.105 mol of 7-amino-3-methoxymethyl-3-cephem-4-carboxylic acid-1-(isopropoxycarbonyloxy)-ethyl ester, obtained analogously as described in Example 1 a), diastereoisomeric ratio (B/A+B) below 0.5, at a temperature of below ca. 5° and further 228 ml of ethyl acetate are added to the mixture obtained. To the mixture obtained the mixture obtained in step a) is added dropwise at a temperature of below 5° within ca. one hour. The temperature is kept below 4°. The mixture obtained (pH 6.2) is stirred for ca. 30 minutes. A two-phase system is obtained, the phases are separated and the organic phase is washed with 370 ml of water. The pH of the organic phase is adjusted to 7.1 by addition of an aqueous sodium bicarbonate solution. The mixture obtained is stirred for ca. 15 minutes and a two-phase system is obtained. The phases are separated and the organic phase is treated with 188 ml of water and 10 ml of 5M aqueous sulphuric acid. The mixture obtained is stirred for ca. 15 minutes and the phases obtained are separated. The organic phase is washed with ca. 200 ml of water and mixed with 117 ml of N,N-dimethylacetamide. The mixture obtained is concentrated in vacuo (rotovapor, 40°/100 mbar) until no further ethyl acetate is distilling off. 7-[2-(2-formylaminothiazol-4-yl)-2-(Z)-(methoxyimino) acetamido]-3-methoxymethy-1-3-cephem-4-carboxylic acid-1-(isopropoxycarbonyloxy)ethyl ester in a diastereoisomeric ratio (B/A+B) of 0.49 is obtained.

The evaporation residue is divided into portions and 7-[2-(2-formylaminothiazol-4-yl)-2-(Z)-(methoxyimino) acetamido]-3-methoxymethyl-3-cephem-4-carboxylic acid-1-(isopropoxycarbonyloxy)ethyl ester is precipitated analogously as described in Example 1 b), but using 33.8 g portions of the evaporation residue instead of 37 g and using an amount of ethanol as set out in TABLE 3 below and an amount of water as set out in TABLE 3 below instead of amounts as set out in TABLE 1 above. 7-[2-(2-formylaminothiazol-4-yl)-2-(Z)-(methoxyimino) acetamido]-3-methoxymethyl-3-cephem-4-carboxylic acid-1-(isopropoxycarbonyloxy)ethyl ester in a diastereoisomeric ratio (B/A+B) and (A/A+B) as set out in TABLE 3 below is obtained:

TABLE 3

| experiment | ml ethanol | ml water | diastereoisomeric ratio (B/A + B) | diastereoisomeric ratio (A/B + A) |
|---|---|---|---|---|
| A | 58.5 | 292.5 | 0.503 | 0.497 |
| B | 58.5 | 146 | 0.518 | 0.482 |
| C | 58.5 | 117 | 0.538 | 0.462 |
| D | 0 | 370 | 0.497 | 0.503 |

EXAMPLE 3 a) 7-Amino-3-methoxymethyl-3-cephem-4-carboxylic Acid-1-(isopropoxycarbonyloxy)ethyl Ester A suspension of 30 g of AMCA in 300 ml of acetone is mixed with 14,2 g of TMG and stirred for 20 minutes at room temperature. The solution obtained is cooled to ca. 0° and mixed over the course of ca. 5 minutes with a solution of 38.0 g of 1-iodoethylisopropyl carbonate in 250 ml of toluene. Stirring is continued for ca. 4 hours at ca. 0° and the solution obtained is poured onto a mixture of 600 ml of water and 20 ml of conc. HCl. The pH of the mixture obtained is adjusted to 1.0. The aqueous phase is extracted with 200 ml of toluene, mixed with 500 ml of methylene chloride and a pH of ca. 8.2 is adjusted by addition of 5N NaOH. A two-phase system is obtained; the organic phase is extracted with water and dried over MgSO$_4$. MgSO$_4$ is filtrated off and washed with with 50 ml of methylene chloride. 590 ml of a solution of 7-amino-3-methoxymethyl-3-cephem-4-carboxylic acid-1-(isopropoxycarbonyloxy) ethyl ester in methylene chloride are obtained (content: 62 g/l). Diastereoisomeric ratio B/(A+B)=0.48; and (A/A+B)= 0.52.

b) Vilsmeier Activation of Z-(2-Formamidothiazol-4-yl)-methoxyimino)-acetic Acid Is carried out analogously as described in Example 2 a) but using 100 ml of methylene chloride instead of 200 ml of ethyl acetate, 27 ml of DMF instead of 54 ml and 13.18 g instead of 26.36 g of (2-N-formylamino-thiazol-4-yl)-methoxyimino)-acetic acid. (Vilsmeier) activated Z-(2-formamidothiazol-4-yl)-methoxyimino)-acetic acid is obtained.

c) 7-[2-(2-Formylaminothiazol-4-yl)-2-(Z)-(methoxyimino)acetamido]-3-methoxymethyl-3-cephem-4-carboxylic Acid-1-(isopropoxycarbonyloxy)ethyl Ester Is carried out analogously as described in Example 2 b) but using 16.8 g of sodiumbicarbonate instead of 33.6 g in 374 ml of water instead of 748 ml of water and adding the mixture to 317 ml of a solution obtained according to example 3 a), containing 0.0525 mol 7-amino-3-methoxymethyl-3-cephem-4-carboxylic acid-1-(isopropoxycarbonyloxy)ethyl ester; and adding 73 ml of methylene chloride instead of 228 ml of ethyl acetate;

and adding the mixture obtained to the mixture containing (Vilsmeier) activated (2-N-formylaminothiazol-4-yl)-methoxyimino)-acetic acid obtained according to Example 3 1) instead to a mixture obtained according to Example 2 a); and using half of the amounts of solvents, water, acid and base after the first phase separation than described in Example 2 b) after the first phase separation, but using DMF instead of dimethylacetamide.

7-[2-(2-formylaminothiazol-4-yl)-2-(Z)-(methoxyimino) acetamido]-3-methoxymethyl-3-cephem-4-carboxylic acid-1-(isopropoxycarbonyloxy)ethyl ester in a diastereoisomeric ratio (B/A+B) of 0.47 is obtained.

To 32.9 g of the evaporation residue are added 58.5 ml of ethanol. To the mixture obtained 105 ml of water are added dropwise. 7-[2-(2-formylaminothiazol-4-yl)-2-(Z)-(methoxyimino)acetamido]-3-methoxymethyl-3-cephem-4-carboxylic acid-1-(isopropoxycarbonyloxy)-ethyl ester in a diastereoisomeric ratio (B/A+B) of 0.50 is obtained.

To 32.9 g of the evaporation residue 370 ml of water is added dropwise. 7-[2-(2-formylaminothiazol-4-yl)-2-(Z)-(methoxyimino)acetamido]-3-methoxymethyl-3-cephem-4-carboxylic acid-1-(isopropoxycarbonyloxy)ethyl ester in a diastereoisomeric ratio (B/A+B) of 0.475 is obtained.

What is claimed is:

1. A process for increasing the diastereoisomeric ratio (B/A+B), wherein B is the more apolar and A is the more polar of the two diastereoisomers, of a mixture of diastereoisomers of a compound of formula

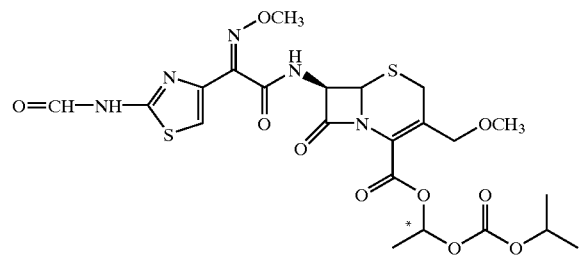

I the diastereoisomers being with respect to the carbon atom marked with a star in formula I, comprising treating a mixture of diastereoisomers of a compound of formula I with alcohol and water and isolating the precipitated compound of formula I in an increased diastereoisomeric ratio (B/A+B) of 0.5 to 0.6.

2. A process according to claim 1, comprising treating a mixture of diastereoisomers of a compound of formula I in an organic amide with alcohol and water.

3. A process according to claim 1, comprising treating a mixture of diastereoisomers of a compound of formula I with alcohol and water in the presence of a compound selected from the group consisting of an amide of formic acid, an amide of acetic acid, a pyrrolidone, a pyrimidinone, an urea and an imidazolidinone.

4. A process according to claim 1 wherein the alcohol is a ($C_{1-6}$) alcohol.

5. A process according to claim 1 wherein a 10 to 50% (w/w) solution of a mixture of diastereoisomers of a compound of formula I in an organic amide is treated with alcohol and water.

6. A process according to claim 5, comprising treating a mixture of diastereoisomers of a compound of formula I with 3 ml to 10 ml alcohol and 10 ml to 30 ml water per gram of a compound of formula I.

7. A process for the production of a mixture of diastereoisomers of cefpodoxime proxetil of formula

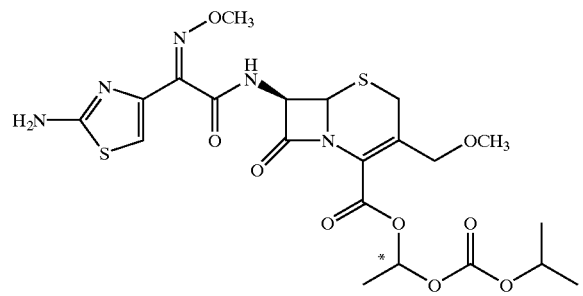

II in a diastereoisomeric ratio (B/A+B), wherein B is the more apolar of the two diastereoisomers, of 0.5 to 0.6, the diastereoisomers being with respect to the carbon atom marked with a star in formula II, comprising producing a mixture of diastereoisomers of a compound of formula

I

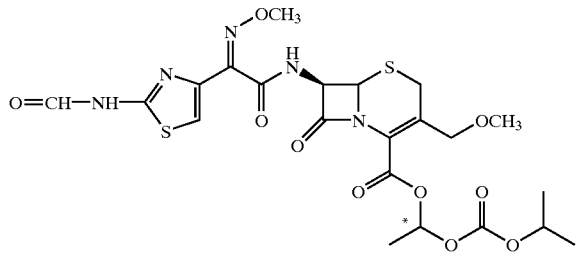

by acylating a compound of formula

III

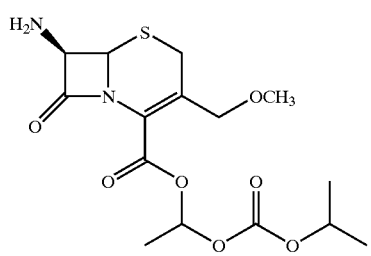

with activated Z-(2-formamidothiazol-4-yl)-methoxyimino acetic acid, treating a mixture of diastereoisomers of a compound of formula I obtained by a process according to claim 1 and splitting off the formyl group from the amino group attached to the thiazolyl group.

8. A process according to claim 7, wherein a compound of formula III is produced by esterifying 7-amino-3-methoxymethyl-3-cephem-4-carboxylic acid with a compound of formula

X—CH—(CH₃)—O—CO—O—CH(CH₃)₂ wherein X denotes a leaving group.

9. A process for the production of a mixture of diastereoisomers of cefpodoxim proxetil of formula II as defined in claim 7 in a diastereoisomeric ratio (B/A+B), wherein B is the more apolar of the two diastereoisomers, of 0.5 to 0.6, the diastereoisomers being with respect to the carbon atom marked with a star in formula II, characterized by the following steps i) esterifying 7-amino-3-methoxymethyl-3-cephem-4-carboxylic acid with a compound of formula

X—CH—(CH₃)—O—CO—O—CH(CH₃)₂ wherein X denotes a leaving group;

ii) acylating the amine group in position 7 of the ring system of a compound of formula III obtained in step i) with activated (2-N-formylamino-thiazol-4-yl)-methoxyimino acetic acid;

iii) adding a compound selected from the group consisting of an amide of formic acid, an amide of acetic acid, a pyrimidinone, an urea and an imidazolidinone to a reaction mixture obtained in step ii) and evaporating off a solvent used in the acylation step, and iv) treating the evaporation residue obtained in step iii) with alcohol and water and isolating the precipitated compound of formula II in a diastereoisomeric ratio (B/A+B) of 0.5 to 0.6.

10. A process for the isolation of 7-[2-(2-formylaminothiazol-4-yl)-2-(Z-(methoxyimino)-acetamido]-3-methoxymethyl-3-cephem-4-carboxylic acid-1-(isopropoxy-carbonyloxy)-ethylester as a diastereoisomeric mixture of formula

I

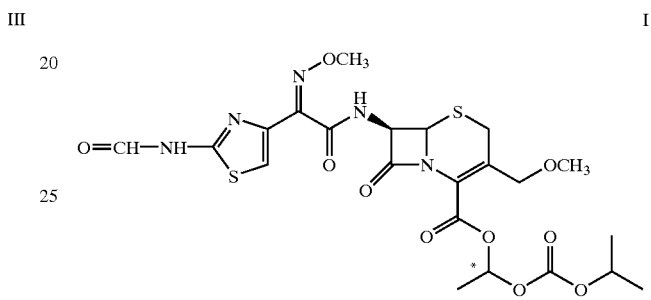

after the reaction of the compound of formula

III

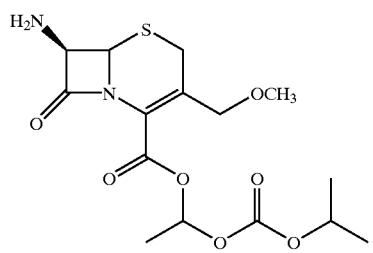

with activated Z-2-(methoxyimino)-2-(2-formylaminothiazol-4-yl)-acetic acid in a solvent, characterized in that to the solution of the compound of formula I is added an amide of acetic acid, an amide of formic acid, or an urea; the solvent is subsequently removed by evaporation and the residue of evaporation is mixed with water and alcohol.

11. The process according to claim 10 wherein the urea is 1,3-dimethyl-2-imidazolidinone (DMEU) or 1,3-dimethyl-3,4,5,6-tetrahydro-2(1H)-pyrimidinone (DMPU).

* * * * *